(12) United States Patent
Moody et al.

(10) Patent No.: US 8,071,330 B2
(45) Date of Patent: Dec. 6, 2011

(54) PROCESS FOR THE SYNTHESIS OF CEFACLOR

(75) Inventors: Harold Monro Moody, Gulpen (NL); Theodorus Johannes Godfried Maria Van Dooren, Leiden (NL)

(73) Assignee: DSM IP Assets B.V., Heerlen (NL)

( * ) Notice: Subject to any disclaimer, the term of this patent is extended or adjusted under 35 U.S.C. 154(b) by 1050 days.

(21) Appl. No.: 11/794,119

(22) PCT Filed: Dec. 23, 2005

(86) PCT No.: PCT/EP2005/057155
§ 371 (c)(1),
(2), (4) Date: Jun. 25, 2007

(87) PCT Pub. No.: WO2004/069984
PCT Pub. Date: Jul. 6, 2006

(65) Prior Publication Data
US 2008/0050771 A1    Feb. 28, 2008

(30) Foreign Application Priority Data

Dec. 27, 2004  (EP) .................................... 04106999

(51) Int. Cl.
*C12P 35/04*    (2006.01)
(52) U.S. Cl. ............................... 435/50; 435/41; 435/47
(58) Field of Classification Search .................. 435/43, 435/44, 35, 36, 47, 50
See application file for complete search history.

(56) References Cited

U.S. PATENT DOCUMENTS 6,287,799 B1 *  9/2001  Van Dooren et al. ........... 435/43

FOREIGN PATENT DOCUMENTS

| EP | 0 730 035 | 9/1996 |
| WO | 98/20120 | 5/1998 |
| WO | 03/055998 | 7/2003 |

OTHER PUBLICATIONS

International Search Report for PCT/EP2005/057155 mail Feb. 22, 2007.

* cited by examiner

*Primary Examiner* — Susan Hanley
(74) *Attorney, Agent, or Firm* — Nixon & Vanderhye P.C.

(57) ABSTRACT

The present invention relates to a process for the synthesis of cefaclor, which process comprises reacting 7-amino-3-chloro cephalosporanic acid (7-ACCA) with D-phenylglycine in activated form (PGa) in the presence of an enzyme in a reaction mixture to form cefaclor, wherein at least part of 7-ACCA and/or PGa are added to the reaction mixture during the course of the reaction. The invention also relates to an aqueous mixture comprising an amount of cefaclor of >10 (w/w) %, an amount of 7-amino-3-chloro cephalosporanic acid of <2 (w/w) %, and an amount of D-phenyl glycine of <2 (w/w) % and a process for the recovery of cefaclor from this aqueous mixture. The invention also relates to cefaclor in crystal form having an absorbance at 400 nm ($A_{400}$) of less than 0.250.

2 Claims, No Drawings

PROCESS FOR THE SYNTHESIS OF CEFACLOR

This application is the US national phase of international application PCT/EP2005/057155 filed 23 Dec. 2005 which designated the U.S. and claims benefit of EP 04106999.8 dated 27 Dec. 2004, the entire content of each of which is hereby incorporated by reference.

The present invention relates to a process for the synthesis of cefaclor, which comprises reacting 7-amino-3-chloro-cephalosporanic acid (7-ACCA) with D-phenylglycine in activated form in the presence of an enzyme, an aqueous mixture comprising cefaclor and a process for the recovery of cefaclor from the aqueous mixture.

A process for the enzymatic synthesis of cefaclor is known from various sources. EP 567 323 discloses a process for the enzymatic synthesis of cefaclor at a temperature of between 0 and 20° C. and an ambient pH at a high molar ratio (5 to 6) of D-phenyl glycine methyl ester to 7-ACCA, which results in a yield of 93% and 88.2%. A high molar ratio of activated side chain to β-lactam nucleus is undesirable since this increases costs involved and by-products formed (eg. D-phenyl glycine) in the enzymatic synthesis reaction, which are difficult to separate from the final antibiotic (cefaclor).

EP 730 035 aims to reduce the molar ratio D-phenyl glycine amide to 7-ACCA in an enzymatic process for the synthesis of cefaclor. By immobilising the enzyme penicillin G amidase on an azlactone polymer, yields of cefaclor per 7-ACCA of 98% and 94% were obtained, wherein the molar ratio D-phenyl glycine amide to 7-ACCA was between 2 and 3.

We found that when the molar ratio of D-phenyl glycine in activated form to 7-ACCA is between about 2 and 3, the amount of by-products formed during the enzymatic synthesis reaction of cefaclor is still too large, which results in processibility problems during the recovery of cefaclor from the reaction mixture, and/or a substantially pure form of cefaclor can not be obtained.

The aim of the present invention is to provide a process for the enzymatic synthesis of cefaclor from 7-ACCA and D-phenyl glycine in activated form, which does not have these drawbacks.

This is achieved according to the invention by a process for the enzymatic synthesis of cefaclor, said process comprising reacting 7-amino-3-chloro-cephalosporanic acid (7-ACCA) with D-phenylglycine in activated form (PGa) in the presence of an enzyme in a reaction mixture to form cefaclor, wherein 7-ACCA and/or PGa are/is added to the reaction mixture during the course of the reaction.

It was surprisingly found that the quantity of cefaclor produced per 7-ACCA in the process for the synthesis of cefaclor according to the invention was higher than in an enzymatic synthesis process wherein the total amount of 7-ACCA and PGa used in the reaction is added at the onset of the reaction.

It was surprisingly found that the conversion of cefaclor in the process for the synthesis of cefaclor according to the invention may be above 90%, preferably above 92%, preferably above 95%, more preferably above 96%.

As used herein, the conversion of cefaclor is defined as the amount of cefaclor (in moles) produced per total amount of 7-ACCA (in moles) added to the reaction mixture.

The yield of cefaclor is defined as the amount of cefaclor (in moles) recovered from the reaction mixture per total amount of 7-ACCA (in moles) added.

In addition it was found that in the process for the synthesis of cefaclor according to the invention a very low amount of by-products was formed. When the concentrations of by-products (eg. D-phenyl glycine) are low in the reaction mixture, it appeared to be possible to recover cefaclor from the reaction mixture in a substantially pure form. A substantially pure form of cefaclor may be defined as a product comprising at least 94 (w/w) %, preferably at least 95 (w/w) %, preferably at least 96 (w/w) %, preferably at least 97 (w/w) % of cefaclor, preferably at least 98% w/w) % of cefaclor, preferably at least 99% w/w) % of cefaclor.

In the process for the synthesis of cefaclor according to the invention, 7-ACCA and PGa preferably are added to the reaction mixture in a molar ratio of PGa to 7-ACCA of below 2, preferably of below 1.8, more preferably of below 1.5, most preferably of below 1.2. It was found that when the molar ratio of PGa to 7-ACCA was maintained below these values, little by-products are formed during the synthesis reaction and very little processibility problems are encountered during the recovery of cefaclor.

As used herein, the molar ratio of PGa to 7-ACCA is defined as the total amount in moles of PGa added to the reaction mixture divided by the total amount in moles of 7-ACCA added to the reaction mixture.

In the process for the enzymatic synthesis of cefaclor according to the invention, 7-ACCA and/or PGa are/is added to the reaction mixture during the course of the reaction. Preferably, at least part of the total amount of 7-ACCA and/or PGa to be added to the reaction mixture are/is added in a continuous or intermittent mode to the reaction mixture in a course of the synthesis reaction of more than 10 min, preferably more than 20 min, preferably more than 30 min, preferably more than 60 min, preferably more than 90 min and preferably less than 360 min, preferably less than 240 min, preferably less than 120 min.

The process for the synthesis of cefaclor according to the invention is preferably a process wherein PGa is added to the reaction mixture during the course of the synthesis reaction. PGa may be added to the reaction mixture in solid form or in solution.

PGa used in the process according to the invention may be an amide, for instance a primary, secondary or tertiary amide, or an ester of D-phenyl glycine. Preferably, PGa is an ester of D-phenyl glycine, for instance a lower alkyl ($C_{1-4}$) ester of D-phenyl glycine, for instance a methyl, ethyl, or isopropyl ester of D-phenyl glycine. Preferred is D-phenyl glycine methyl ester (PGM), and most preferred PGM in the form of a salt, for example a formic acid, methane sulphonic acid or HCl salt of PGM. A formic acid, methane sulphonic acid, or HCl salt of other D-phenyl glycine esters may also be used.

Any enzyme may be used that is suitable as a catalyst in reacting 7-ACCA with PGa to prepare cefaclor in the process according to the invention. Such enzymes are for instance the enzymes that are known under the general term penicillin acylase, or penicillin G acylase, also called penicillin G amidase or benzylpenicillin acylase (EC 3.5.1.11). Penicillin G acylase refers to a group of hydrolases from microorganisms, especially bacteria, capable of hydrolysing the 6-acyl group of penicillins or the 7-acyl group of cephalosporins. Penicillin acylase enzymes may be classified both on the basis of their substrate specificity and on the basis of their molecular structure, which is described in various publications, see for instance WO 03/055998 and WO 98/20120.

Microorganisms from which penicillin acylase enzymes may be obtained are for example *Acetobacter*, in particular *Acetobacter pasteurianum, Aeromonas, Alcaligenes*, in particular *Alcaligenes faecalis, Aphanocladium, Bacillus* sp., in particular *Bacillus megaterium, Cephalosporium, Escherichia*, in particular *Escherichia coli, Flavobacterium, Fusarium*, in particular *Fusarium oxysporum* and *Fusarium*

*solani, Kluyvera, Mycoplana, Protaminobacter, Proteus*, in particular *Proteus rettgari, Pseudomonas* and *Xanthomonas*, in particular *Xanthomonas citrii*.

In a preferred embodiment of the present invention the enzyme in the process for the synthesis of cefaclor is a mutant enzyme.

A mutant of penicillin acylase or an acylase mutant, can be made by starting from any known penicillin acylase. A mutated acylase is for example derived from wild-type acylases via recombinant DNA methodology known in the art, by substituting one amino acid residue for a new residue.

The mutant penicillin acylase used in the process according to the invention may for example be a penicillin acylase having a higher S/H ratio than the wild-type acylase of *E. coli*.

As defined herein, the synthesis/hydrolysis (S/H) ratio is understood to be the molar ratio of synthesis product to hydrolysis product at a particular moment during the enzymatic reaction. Synthesis product is understood to be the β-lactam antibiotic formed from the activated side chain and β-lactam nucleus. Hydrolysis product is understood to be the corresponding acid of the activated side chain.

The S/H ratio is a function of the concentration of the reactants, the molar ratio of activated side chain to β-lactam nucleus, the temperature, the pH and the enzyme. In the ideal situation a comparative experiment is carried out where the particular candidate is tested against a reference enzyme, preferably *E. coli* PenG acylase, under the same conditions. A detailed description of how a S/H ratio can be determined is given in WO 03/055998.

Preferably, the mutant enzyme is a mutant penicillin acylase having an amino acid substitution at position 24 of the β-subunit corresponding to the β-subunit of penicillin acylase of *E. coli*. In a preferred embodiment, the L-phenyl-alanine at position 24 of the β-subunit corresponding to the β-subunit of penicillin acylase of *E. coli*, has been replaced in that position by L-alanine, as is described in WO 98/20120. This mutation can be applied on a Pen G acylase from *E. coli*, but Pen G acylases from other sources may also by used. The numbering of the position of the amino acids corresponds to the numbering of the amino acid sequence of wild type Penicillin G acylase of *E. coli*.

In a further preferred embodiment of the invention the enzyme may be immobilised on a carrier. In immobilised form the enzyme can be readily separated and recycled. Immobilised enzymes are known as such and are commercially available, for example an *E. coli* penicillin acylase isolated as described in WO 92/12782 and immobilised as described in EP 222 462 and in WO97/04086.

The process for the synthesis of cefaclor according to the invention may be carried out at any suitable pH. Preferably, the enzymatic synthesis reaction is carried out at a pH of between 6 and 8, preferably between 6.5 and 7.7, more preferably between 6.8 and 7.2. The pH of the reaction mixture may be adjusted to the right pH value with any organic or inorganic suitable base, or any suitable organic or inorganic acid.

The process for the synthesis of cefaclor according to the invention may be carried out at any suitable temperature. Preferably, the enzymatic synthesis reaction is carried out at a temperature of between 5 and 35° C., preferably between 8 and 25° C., more preferably between 18 and 23° C. The enzymatic synthesis reaction may also be carried out at a temperature of between 8 and 16° C., preferably, between 9 and 15° C., preferably between 10 and 14° C.

The reaction mixture in the process for the enzymatic synthesis of cefaclor is in principle an aqueous reaction mixture. The aqueous reaction mixture may contain an organic solvent or a mixture of organic solvents, preferably less than 30 vol %, more preferably less than 20 vol. %, more preferably less than 10 vol. %, more preferably less than 5 vol. % (relative to the total volume of the liquid). Preferably, the organic solvent is an alcohol with 1-7 carbon atoms, for instance a monoalcohol, in particular methanol or ethanol; a diol, in particular ethylene glycol, or a triol, in particular glycerol. Preferably, the aqueous reaction mixture contains at least 70 vol. % water, more preferably at least 80 vol. %, more preferably at least 90 vol. %, most preferably at least 95 vol. % water (relative to the sum volume of the liquid).

At the end of the enzymatic synthesis reaction, the temperature of the reaction mixture may be lowered to a temperature of below 5° C., preferably below a temperature of below 4° C., and preferably above 0° C.

At the end of the enzymatic synthesis reaction the cefaclor formed may be recovered from the aqueous reaction mixture, for example by centrifugation or filtration.

The present invention also relates to an aqueous mixture comprising cefaclor, 7-amino-3-chloro cephalosporanic acid (7-ACCA) and D-phenyl glycine (PG), wherein the aqueous mixture comprises an amount of cefaclor of >10 (w/w) %, an amount of 7-ACCA of <2 (w/w) %, and an amount PG of <2 (w/w) %. This aqueous mixture may advantageously be obtained by the process for the synthesis of cefaclor according to the invention. Preferably, the aqueous mixture comprises an amount of cefaclor of >12 (w/w) %, more preferably >15 (w/w) %; preferably the amount of cefaclor in the aqueous mixture is <50 (w/w) %, more preferably <30 (w/w) %. Preferably, the aqueous mixture comprises an amount of 7-ACCA of <1.5 (w/w) %, more preferably <1 (w/w) %, more preferably <0.8 (w/w) %, more preferably <0.6 (w/w) %, more preferably <0.4 (w/w) %. Preferably, the aqueous mixture comprises an amount of PG of <1.5 (w/w) %, preferably of <1.2 (w/w) %, more preferably of <1 (w/w) %, more preferably of <0.8 (w/w) %. It was surprisingly found that cefaclor could be easily recovered from the aqueous mixture according to the invention, in a substantially pure form, with little or no processibility problems.

The invention also relates to a process for the recovery of the cefaclor from the aqueous mixture according to the invention, for example by centrifugation or filtration. Preferably, cefaclor is recovered from the aqueous mixture through a bottom sieve with up-wards stirring (see for instance NL 1006267), resulting in a suspension comprising cefaclor crystals.

The aqueous mixture according to the invention or a suspension comprising cefaclor crystals may be acidified to a pH of between 0.5 and 2, resulting in an acid solution comprising dissolved cefaclor. Acidifying to a pH of between 0.5 and 2 may be carried out with any suitable inorganic acid, such as hydrochloric acid, nitric acid, and sulphuric acid or any suitable organic acid, such as formic acid, acetic acid, and citric acid. Preferably, hydrochloric acid is used to acidify the aqueous mixture according to the invention or the suspension comprising cefaclor crystals, resulting in an acid solution comprising dissolved cefaclor.

The aqueous mixture according to the invention or the acid solution comprising dissolved cefaclor may be brought to a pH of between 4 and 6, whereby cefaclor crystals are formed. Suitable bases to bring the aqueous mixture according to the invention or the acid solution comprising dissolved cefaclor to a pH of between 4 and 6 are inorganic bases, such as ammonia, sodium or potassium hydroxide, or organic bases, such as triethylamine or guanidine. Preferably, ammonia is used to bring an acid solution comprising dissolved cefaclor to a pH of between 4 and 6.

The cefaclor may crystallised in any suitable form, typically in the form of cefaclor hydrate, for instance cefaclor monohydrate.

The cefaclor crystals formed by bringing the acid solution comprising dissolved cefaclor to a pH of between 4 and 6, may be separated from the solution by any method known in the art, for instance by centrifugation or filtration, resulting in a wet cake comprising cefaclor crystals.

The wet cake comprising the cefaclor crystals may subsequently be washed and dried by any method known in the art.

Surprisingly, it was found that cefaclor crystals obtained by the process for obtaining cefaclor from the aqueous mixture according to the present invention resulted in cefaclor crystals with a low coloration. Preferably, the cefaclor crystals with low coloration are obtained from an aqueous mixture obtained by the process for the enzymatic synthesis of cefaclor according to the invention.

In the scope of the present invention a low coloration of cefaclor crystals may be defined as a low absorbance at 400 nm, for instance an absorbance at 400 nm of below 0.250.

Accordingly, in one embodiment the invention relates to cefaclor in crystal form having an absorbance at 400 nm ($A_{400}$) of less than 0.250, preferably less than 0.200, preferably less than 0.150, preferably less than 0.100, preferably less than 0.090, preferably less than 0.080, preferably less than 0.070, preferably less than 0.060, preferably less than 0.050, by measuring the $A_{400}$ of a solution of 0.5 g of the cefaclor in crystal form dissolved in 10 ml 1 N HCl solution, after 90 s at room temperature.

Cefaclor may be stabilised by the presence of a complexing agent. A complexing agent may be added to the reaction mixture during the synthesis reaction, or may be added to the reaction mixture after the synthesis reaction has completed or to the aqueous mixture according to the invention. A complexing agent may also be added during the process for recovering of cefaclor. Suitable complexing agents may be naphtalenes, chinolines, anthrachinonsulphonic acids or parabenes. Examples of complexing agents are 1-naphtol, 2-naphtol, 2,6-dihydroxynaphtalene, and anthrachinon-1,5-disulphonic acid.

The following examples illustrate the invention and are not to be construed as being limited thereto.

EXAMPLES

Enzyme and Immobilisation

The penicillin acylase as used herein was an *E. coli* PenG acylase mutant Phe-B24-Ala, as described in WO 98/20120. The enzyme was immobilised as described in EP 222 462 and WO-A-97/04086, with gelatin and chitosan being used as gelling agent and glutaraldehyde as cross-linker.

Example 1 a) Enzymatic Synthesis of Cefaclor

A reactor with 175 μm sieve bottom was filled with 5.0 g immobilised PenG acylase mutant Phe-B24-Ala. 13.9 g (58.1 mmol) 7-ACCA, 0.1 g sodium sulphite and 60 g water were added at 20° C. and the pH was adjusted to 7.0 with ammonia.

In a separate vessel a PGM solution was prepared by mixing 12.9 g (63.8 mmol) PGM HCl salt and 21 g water at 20° C.

The PGM solution was dosed into the reactor at a constant rate from t=0 to t=117 min. The enzymatic condensation reaction started at t=0, when the first PGM solution was dosed. The pH was maintained at 7.0 with ammonia.

At t=150 min, the concentrations of cefaclor, 7-ACCA, PGM and PG were 17.5 (w/w) %, 0.33 (w/w) %, 0.23 (w/w) % and 0.79 (w/w) %, respectively.

At t=150 min the conversion into cefaclor was 97.0% per 7-ACCA added and the S/H ratio was 9.1.

Subsequently, the pH was decreased to 5.3 with a hydrochloric acid solution. The temperature was decreased to 2° C.

b) Recovery of Cefaclor

The reactor was discharged through a bottom sieve with upwards stirring. The resulting cefaclor suspension was filtered through a glass filter. The resulting mother liquor was transferred back into the reactor. This sequence of steps was repeated five times. In this way, >95% of solid cefaclor was separated from the solid biocatalyst.

The cefaclor wet cake and mother liquor were combined, and the temperature was maintained at 2° C. The pH of the combined cefaclor wet cake and mother liquor was decreased to 0.8 with hydrochloric acid and the resulting solution was filtered through a 0.45 μm filter.

A crystallisation reactor was filled with 34 g water and 1.0 g cefaclor as seed. The above-mentioned acidic cefaclor solution was dosed into the crystallisation reactor in 60 minutes at 35° C. The pH was kept at 5.0 with ammonia. Subsequently, the temperature was lowered in steps: 30 min at 30° C., 30 min at 25° C., and 60 min at 20° C. The suspension was filtered through a glass filter and the wet cake was washed with one volume of water and two volumes of acetone. After drying, 15.7 g cefaclor monohydrate was obtained (purity 99.4%).

Comparative Example a) Enzymatic Synthesis of Cefaclor

A reactor with 175 μm sieve bottom was filled with 5.0 g immobilised PenG acylase mutant Phe-B24-Ala. 13.9 g (58.1 mmol) 7-ACCA, 0.1 g sodium sulphite and 81 g water were added at 20° C. and the pH was adjusted to 7.0 with ammonia. 12.9 g (63.8 mmol) PGM HCl salt was added at to the reactor, which started the enzymatic condensation reaction. The pH was maintained at 7.0 with ammonia.

A very viscous, sorbet-like suspension was formed.

At t=150 min, the concentrations of cefaclor, 7-ACCA, PGM and PG were 10.5%, 4.71%, 0.11% and 3.96%, respectively. The conversion into cefaclor was 59% with regard to 7-ACCA, and the S/H ratio was 1.1.

Subsequently, the pH was decreased to 5.3 with hydrochloric acid solution. The temperature was decreased to 2° C.

b) Recovery of Cefaclor

An attempt was made to discharge the reactor through the bottom sieve with upwards stirring. However, it was not possible to separate the cefaclor suspension from the immobilised biocatalyst, due to the very high viscosity.

Example 2 a) Enzymatic Synthesis of Cefaclor

A reactor with 175 μm sieve bottom was filled with 10.0 g immobilised PenG acylase mutant Phe-B24-Ala. 13.9 g (58.1 mmol) 7-ACCA and 52.5 g water were added at 10° C. and the pH was adjusted to 7.0 with ammonia.

In a separate vessel, PGM solution was prepared by mixing 16.7 g (63.7 mmol) PGM methane sulphonic acid (MSA) salt and 20 g water at 10° C.

The PGM solution was dosed into the reactor at a constant rate from t=0 to t=90 min. The enzymatic condensation reaction started at t=0, when the first PGM solution was dosed. The pH was maintained at 7.0 with ammonia. The temperature was kept at 12° C. From t=120 to t=180 min, the temperature was linearly decreased from 12 to 2° C.

At t=190 min, the concentrations of cefaclor, 7-ACCA, PGM and PG were 18.1 (w/w) %, 0.20 (w/w) %, 0.04 (w/w) % and 0.64 (w/w) %, respectively.

At t=190 min the conversion cefaclor produced was 98.0% per 7-ACCA added and the S/H ratio was 12.

Subsequently, the pH was decreased to 5.0 with a hydrochloric acid solution.

b) Recovery of Cefaclor

The reactor was discharged through a bottom sieve with upwards stirring. The resulting cefaclor suspension was filtered through a glass filter. The resulting mother liquor was transferred back into the reactor. This sequence of steps was repeated five times. Subsequently, the enzyme was washed with 2×10 ml water. In this way, ≧95% of cefaclor was separated from the solid biocatalyst.

The cefaclor wet cake, mother liquor and wash water were combined, and the temperature was maintained at 2° C. The pH of the combined cefaclor wet cake and mother liquor was decreased to 0.5 with hydrochloric acid and the resulting solution was filtered through a 0.45 µm filter.

A crystallisation reactor was filled with 10 g water. The above-mentioned acidic cefaclor solution was dosed into the crystallisation reactor in 30 minutes at 25° C. The pH was kept at 5.0 with ammonia. Subsequently, the suspension was stirred at 10° C. for another 30 min. The suspension was filtered through a glass filter and the wet cake was washed with 2×15 ml water and 2×15 ml acetone. After drying, 18.3 g cefaclor monohydrate was obtained (purity 99.6%).

Example 3

Coloration of Cefaclor

The coloration of cefaclor monohydrate obtained from Example 2 was determined by measuring the absorbance at 400 nm.

0.5 g of cefaclor monohydrate was dissolved in 10 ml 1 N HCl solution. The absorbance was determined at 400 nm (=$A_{400}$) on a Perkin Elmer 550 S spectrophotometer at room temperature, against 1 N HCl solution as a reference solution. The $A_{400}$ was determined after 90 s. The absorbance of cefaclor monohydrate measured directly after isolation and drying as described in Example 2, was 0.036. After 4 weeks storage of cefaclor monohydrate crystals from Example 2 at room temperature and 70% relative humidity the absorbance of cefaclor monohydrate was 0.043.

The invention claimed is:

1. A process for the synthesis of cefaclor, said process comprising reacting 7-amino -3-chloro cephalosporanic acid (7-ACCA) and a mutant penicillin acylase of *E. coli* having a beta subunit wherein said mutant penicillin acylase has L-alanine substituted for L-phenylalanine at position 24 of the beta-subunit with added D-phenylglycine methyl ester in a reaction mixture at a pH of 7 to form cefaclor, wherein the added D-phenylglycine methyl ester is added at a constant rate for at least 90 minutes to the reaction mixture during the course of the reaction, wherein the added D-phenyl glycine methyl ester is added in a total amount to the reaction mixture in a 1.1 molar ratio to the 7-ACCA .

2. The process according to claim 1, wherein the synthesis reaction is carried out at a temperature of between 5 and 35° C.

* * * * *